US011436726B2

United States Patent
Kamon (10) Patent No.: US 11,436,726 B2
(45) Date of Patent: Sep. 6, 2022

(54) MEDICAL IMAGE PROCESSING SYSTEM (71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/169,525

(22) Filed: Feb. 7, 2021

(65) Prior Publication Data

US 2021/0158520 A1  May 27, 2021

Related U.S. Application Data (63) Continuation of application No. PCT/JP2019/032275, filed on Aug. 19, 2019.

(30) Foreign Application Priority Data

Aug. 20, 2018 (JP) .............................. JP2018-154054

(51) Int. Cl.
*G06T 7/00* (2017.01)
*G06T 11/60* (2006.01)

(52) U.S. Cl.
CPC ............ *G06T 7/0012* (2013.01); *G06T 11/60* (2013.01); *G06T 2207/10068* (2013.01)

(58) Field of Classification Search
CPC ................... G06T 7/0012; G06T 11/60; G06T 2207/10068; G06T 11/00; A61B 1/000094; A61B 1/00045
See application file for complete search history.

(56) References Cited

U.S. PATENT DOCUMENTS

| | | | | |
|---|---|---|---|---|
| 6,620,103 B1 * | 9/2003 | Bruce | ................ | G01S 7/52039 600/458 |
| 2011/0254937 A1 * | 10/2011 | Yoshino | ............. | A61B 1/00055 348/E7.085 |
| 2012/0128264 A1 * | 5/2012 | Yazdanfar | ............ | A61B 5/0059 382/274 |
| 2012/0274754 A1 | 11/2012 | Tsuruoka | | |
| 2013/0069945 A1 * | 3/2013 | Ledesma Carbayo | ....................... | A61B 90/36 345/420 |

(Continued)

FOREIGN PATENT DOCUMENTS

| | | |
|---|---|---|
| JP | 2011160848 | 8/2011 |
| WO | 2013144841 | 10/2013 |

(Continued)

OTHER PUBLICATIONS

"International Search Report (Form PCT/ISA/210) of PCT/JP2019/032275," dated Nov. 12, 2019, with English translation thereof, pp. 1-3.

(Continued)

*Primary Examiner* — Maria E Vazquez Colon
(74) *Attorney, Agent, or Firm* — JCIPRNET (57) ABSTRACT

A region-of-interest detection unit detects a region of interest from a medical image. A display control unit keeps displaying a detection result of the region of interest for a certain period of time on a monitor, in a case where a position of the region of interest is changed in accordance with a movement of the region of interest, at a detection position of the region of interest detected by the region-of-interest detection unit before the position of the region of interest is changed.

12 Claims, 10 Drawing Sheets

(56) References Cited

U.S. PATENT DOCUMENTS

| | | | |
|---|---|---|---|
| 2013/0257910 A1* | 10/2013 | Park | G06K 9/00 |
| | | | 382/128 |
| 2015/0257635 A1 | 9/2015 | Kubo et al. | |
| 2018/0242817 A1* | 8/2018 | Imaizumi | A61B 1/00055 |
| 2018/0249900 A1* | 9/2018 | Imaizumi | A61B 1/045 |
| 2019/0114738 A1* | 4/2019 | Sonoda | G06T 3/4023 |
| 2020/0065970 A1* | 2/2020 | Sonoda | A61B 1/000094 |

FOREIGN PATENT DOCUMENTS

| | | |
|---|---|---|
| WO | 2014084134 | 6/2014 |
| WO | 2017216922 | 12/2017 |

OTHER PUBLICATIONS

"Written Opinion of the International Searching Authority (Form PCT/ISA/237) of PCT/JP2019/032275," dated Nov. 12, 2019, with English translation thereof, pp. 1-9.

"Search Report of Europe Counterpart Application", dated Sep. 15, 2021, p. 1-p. 6.

* cited by examiner

MEDICAL IMAGE PROCESSING SYSTEM

CROSS-REFERENCE TO RELATED APPLICATIONS

This application is a Continuation of PCT International Application No. PCT/JP2019/032275 filed on 19 Aug. 2019, which claims priority under 35 U.S.C § 119(a) to Japanese Patent Application No. 2018-154054 filed on 20 Aug. 2018. The above application is hereby expressly incorporated by reference, in its entirety, into the present application.

BACKGROUND OF THE INVENTION

1. Field of the Invention

The present invention relates to a medical image processing system using an analysis result of a medical image.

2. Description of the Related Art

In the current medical field, medical image processing systems using medical images, such as an endoscope system including a light source device, an endoscope, and a processor device, are widely used. In recent years, diagnostic information regarding the state of a disease has been acquired by extracting a region of interest containing a potential lesion portion from a medical image and performing image analysis on the extracted region of interest.

For example, in WO2017/216922A (corresponding to US2019/0114738A1), an image of a region of interest detected from a medical image is stored, and the stored image of the region of interest is displayed in a part different from a part to be observed displaying the medical image at a timing at which the detection of the region of interest on the medical image is interrupted/ceased. In JP2011-160848A (corresponding to US2012/0274754A1), when a region of interest is detected, alert information indicating the detection of the region of interest is displayed for a certain period of time.

SUMMARY OF THE INVENTION

As disclosed in JP2011-160848A, displaying the alert information for a certain period of time can prevent a user from overlooking the region of interest. In a case where the region of interest appears for a moment in a medical image, displaying the alert information can prevent the region of interest from being overlooked. However, the alert display is displayed over the entire peripheral portion of the medical image, and it is not possible to grasp in which direction the region of interest has disappeared. Since it takes time for the user to grasp the direction of disappearance of the region of interest, it may not be possible to ensure that diagnosis is performed.

It is an object of the present invention to provide a medical image processing system capable of preventing, when detecting a region of interest from a medical image, the region of interest from being overlooked and capable of grasping, even if the region of interest has disappeared from the medical image, the direction of disappearance of the region of interest.

A medical image processing system of the present invention includes a medical image acquisition unit, a region-of-interest detection unit, and a display control unit. The medical image acquisition unit acquires a medical image obtained by imaging of an observation target. The region-of-interest detection unit detects a region of interest from the medical image. The display control unit keeps displaying a detection result of the region of interest for a certain period of time on a display unit, in a case where a position of the region of interest is changed in accordance with a movement of the region of interest, at a detection position of the region of interest detected by the region-of-interest detection unit before the position of the region of interest is changed.

Preferably, the display control unit keeps displaying the detection result of the region of interest for a certain period of time at a specific detection position among detection positions of the region of interest. Preferably, the display control unit changes a display style of the detection result of the region of interest according to a timing at which the region of interest is detected.

Preferably, the display style of the detection result of the region of interest is a region-of-interest geometric shape representing the detection result of the region of interest as a geometric shape including at least the region of interest, and the display control unit changes a display style of the region-of-interest geometric shape according to a timing at which the region of interest is detected. Preferably, the display style of the region-of-interest geometric shape includes a shape, a size, or a color of the region-of-interest geometric shape or a line of the region-of-interest geometric shape.

Preferably, the display style of the detection result of the region of interest is region-of-interest highlighting for highlighting the region of interest, and the display control unit changes a degree of highlighting for the region-of-interest highlighting according to a timing at which the region of interest is detected. Preferably, the region-of-interest highlighting includes pseudo-color highlighting for highlighting the region of interest in pseudo-color, and the display control unit changes the degree of highlighting for the region-of-interest highlighting or a proportion of a color component of the region-of-interest highlighting according to a timing at which the region of interest is detected.

Preferably, the display control unit displays the detection result of the region of interest in at least one of a first display region of the display unit that displays the medical image or a second display region different from the first display region of the display unit that displays the medical image. Preferably, a display style of the detection result of the region of interest displayed in the first display region is identical to or different from a display style of the detection result of the region of interest displayed in the second display region. Preferably, the display control unit displays the detection result of the region of interest in a portion of an outer peripheral portion of a first display region of the display unit that displays the medical image, the portion of the outer peripheral portion being a portion corresponding to the detection position of the region of interest.

According to the present invention, it is possible to prevent, when detecting a region of interest from a medical image, the region of interest from being overlooked, and to grasp, even if the region of interest has disappeared from the medical image, the direction of disappearance of the region of interest.

BRIEF DESCRIPTION OF THE DRAWINGS

FIG. 1 is a block diagram illustrating an image processing system, an endoscope system, and so on;

DESCRIPTION OF THE PREFERRED EMBODIMENTS

First Embodiment

Figure 1:
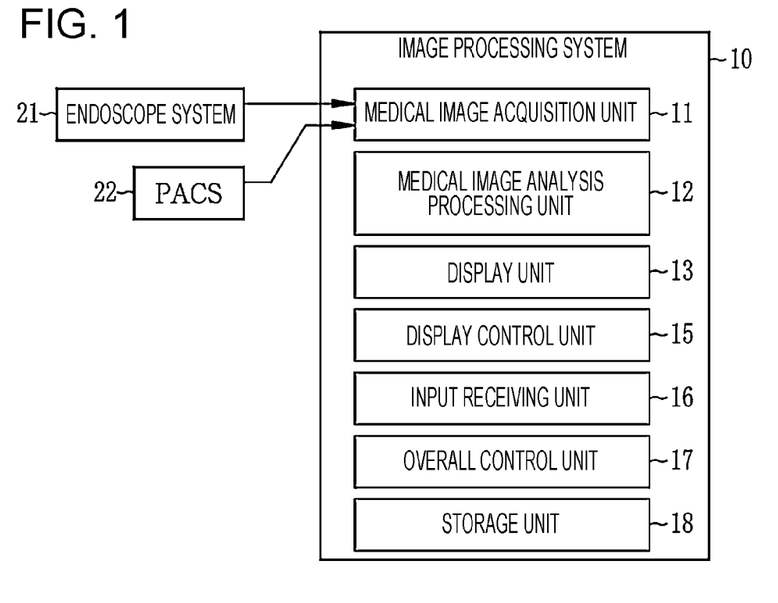

As illustrated in FIG. 1, an image processing system 10 includes a medical image acquisition unit 11, a medical image analysis processing unit 12, a display unit 13, a display control unit 15, an input receiving unit 16, an overall control unit 17, and a storage unit 18.

The medical image acquisition unit 11 acquires a medical image including a photographic subject image directly from an endoscope system 21 or the like that is a medical apparatus, or via a management system such as a PACS (Picture Archiving and Communication System) 22 or any other information system. The medical image is a still image or a moving image (so-called examination moving image). When the medical image is a moving image, the medical image acquisition unit 11 can acquire, as still images, frame images constituting the moving image after an examination. When the medical image is a moving image, furthermore, displaying the medical image includes displaying a still image of one representative frame constituting the moving image, and reproducing the moving image one or a plurality of times. The medical image acquired by the medical image acquisition unit 11 includes an image captured by a doctor using a medical apparatus such as the endoscope system 21, and an image automatically captured by the medical apparatus such as the endoscope system 21 regardless of an image-capturing instruction given by the doctor. In this embodiment, since the image processing system 10 and the endoscope system 21 perform image processing using a medical image, both the image processing system 10 and the endoscope system 21 correspond to a medical image processing system. The medical image system also includes an ultrasound diagnostic apparatus that acquires and displays an image in real time.

When a plurality of medical images can be acquired, the medical image acquisition unit 11 can selectively acquire one or a plurality of medical images among these medical images. Further, the medical image acquisition unit 11 can acquire a plurality of medical images acquired in a plurality of different examinations. For example, the medical image acquisition unit 11 can acquire either or both of a medical image acquired in an examination performed in the past and a medical image acquired in the latest examination. That is, the medical image acquisition unit 11 can arbitrarily acquire a medical image.

In this embodiment, a plurality of medical images including photographic subject images are acquired. More specifically, in a case where a medical image captured in a single specific examination is acquired and there is a plurality of medical images captured in a single specific examination, a plurality of medical images are acquired from among the series of medical images. In this embodiment, furthermore, the image processing system 10 is connected to the endoscope system 21 to acquire a medical image from the endoscope system 21. That is, in this embodiment, a medical image is an endoscopic image.

The display unit 13 is a display that displays the medical image acquired by the medical image acquisition unit 11 and an analysis result obtained by the medical image analysis processing unit 12. A monitor or display included in a device to which the image processing system 10 is connected can be shared and used as the display unit 13 of the image processing system 10. The display control unit 15 controls a display style of the medical image and the analysis result on the display unit 13.

The input receiving unit 16 accepts an input from a mouse, a keyboard, or any other operating device connected to the image processing system 10. The operation of the units of the image processing system 10 can be controlled using these operating devices.

The overall control unit 17 performs overall control of the operation of the units of the image processing system 10.

When the input receiving unit 16 receives an operation input using an operating device, the overall control unit 17 controls the units of the image processing system 10 in accordance with the operation input.

The storage unit 18 stores a still image or the like of a medical image in a storage device (not illustrated) such as a memory included in the image processing system 10 or in a storage device (not illustrated) included in the medical apparatus such as the endoscope system 21 or the PACS 22.

Figure 2:
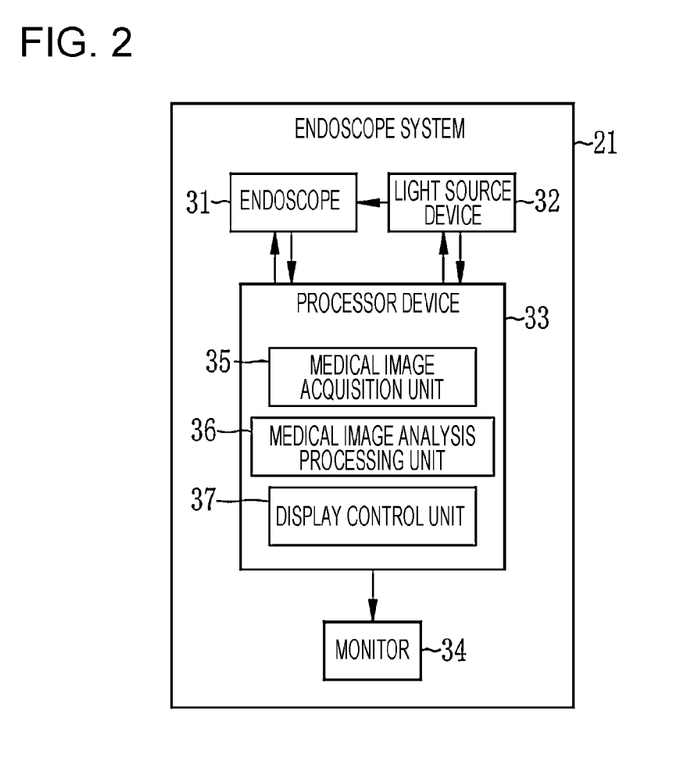
FIG. 2 is a block diagram illustrating the endoscope system.

As illustrated in FIG. 2, in this embodiment, the endoscope system 21 to which the image processing system 10 is connected includes an endoscope 31 that captures an image of a photographic subject irradiated with at least one of light in the white wavelength range or light in a specific wavelength range to acquire an image, a light source device 32 that irradiates the inside of the photographic subject with illumination light via the endoscope 31, a processor device 33, and a monitor 34 that displays a medical image such as an endoscopic image captured using the endoscope 31. The light in the specific wavelength range to be used as illumination light by the endoscope 31 is, for example, light in a shorter wavelength range than the green wavelength range and is, in particular, light in the blue range or violet range in the visible range.

The processor device 33 includes a medical image acquisition unit 35, a medical image analysis processing unit 36, and a display control unit 37. The medical image acquisition unit 35 acquires the medical image output from the endoscope 31. The medical image analysis processing unit 36 performs analysis processing on the medical image acquired by the medical image acquisition unit 35. The content of the processing performed by the medical image analysis processing unit 36 is similar to the content of the processing performed by the medical image analysis processing unit 12 of the image processing system 10. The display control unit 37 displays the medical image obtained by the medical image analysis processing unit 36 on the monitor 34 (display unit). The processor device 33 is connected to the image processing system 10. The medical image acquisition unit 35 is similar to the medical image acquisition unit 11, the medical image analysis processing unit 36 is similar to the medical image analysis processing unit 12, and the display control unit 37 is similar to the display control unit 15.

Figure 3:
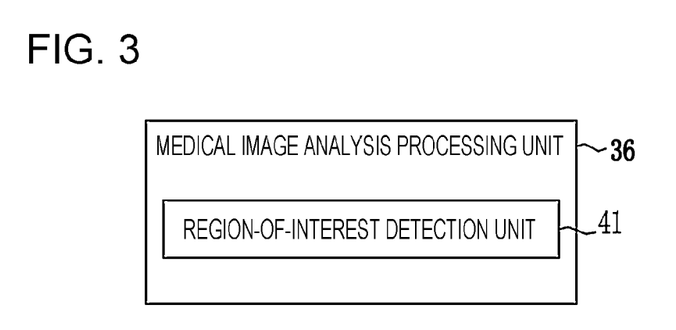
FIG. 3 is a block diagram illustrating the functions of a medical image analysis processing unit.

The medical image analysis processing unit 36 performs analysis processing using the medical image acquired by the medical image acquisition unit 35. As illustrated in FIG. 3, the medical image analysis processing unit 36 includes a region-of-interest detection unit 41. The region-of-interest detection unit 41 performs region-of-interest detection processing for detecting a region of interest from the medical image. Examples of the region-of-interest detection processing include NN (Neural Network), CNN (Convolutional Neural Network), AdaBoost, and random forest. Alternatively, the region-of-interest detection processing may involve detecting a region of interest on the basis of a feature value obtained as color information of the medical image, the gradient of pixel values, or the like. The gradient of pixel values or the like changes according to, for example, the shape of the photographic subject (such as generalized ups and downs or localized depression or elevation in a mucous membrane), color (color such as from inflammation, bleeding, redness, or whitening caused by atrophy), tissue characteristics (such as the thickness, depth, or density of blood vessels, or a combination thereof), structural characteristics (such as pit pattern), or the like.

The region of interest detected by the region-of-interest detection unit 41 is a region including, for example, a lesion portion such as a cancer, a benign tumor portion, an inflammation portion (including, in addition to so-called inflammations, a portion with a change such as bleeding or atrophy), a colon diverticulum, a treatment mark (an EMR (Endoscopic mucosal resection) scar, an ESD (Endoscopic Submucosal Dissection) scar, or a clip location), a bleeding point, a perforated hole, a vascular anomaly, an ablation mark by heating, a marking portion marked by coloring with a coloring agent, a fluorescent agent, or the like, or a biopsy-performing portion subjected to a biopsy. That is, a region including a lesion, a region of a potential lesion, a region subjected to some treatment such as a biopsy, a treatment tool such as a clip or forceps, a region requiring detailed observation regardless of the possibility of a lesion, such as a dark region (a region where observation light is difficult to reach because of the back of the fold or the back of the lumen), or the like can be a region of interest. In the endoscope system 21, the region-of-interest detection unit 41 detects, as a region of interest, a region including at least one of a lesion portion, a benign tumor portion, an inflammation portion, a colon diverticulum, a treatment mark, a bleeding point, a perforated hole, a vascular anomaly marking portion, or a biopsy-performing portion.

Figure 4:
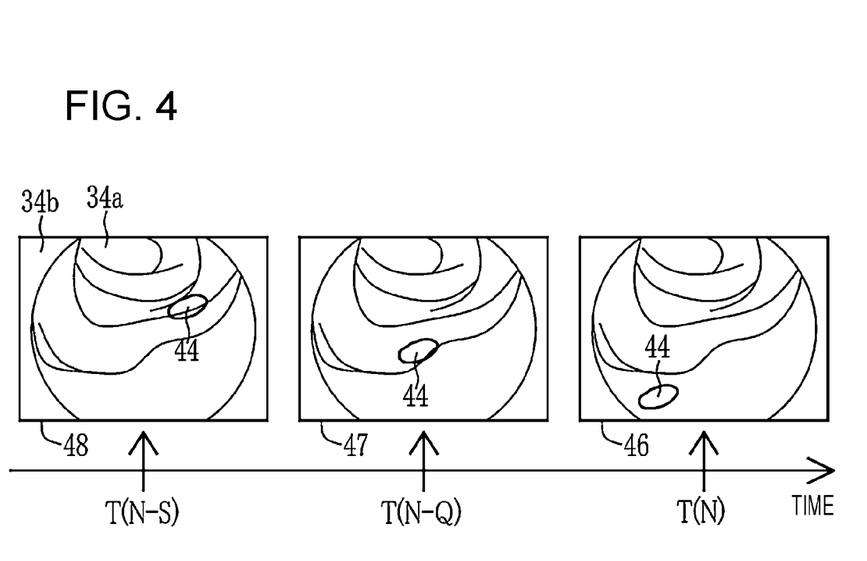
FIG. 4 is an explanatory diagram illustrating medical images at a timing T(N), a timing T(N-Q), and a timing T(N-S)

A region-of-interest detection result indicating that the region-of-interest detection unit 41 has detected the region of interest is displayed on the monitor 34 by the display control unit 37. In this embodiment, as illustrated in FIG. 4, in a case where an identical region of interest 44 moves from the upper right to the lower left in a first display region 34a of the monitor 34 through a center portion along with the passage of time, region-of-interest detection results are displayed such that the movement path of the region of interest 44 can be found. A medical image 46 at a timing (N) is the latest image. A medical image 47 at a timing T(N-Q) is an image acquired at a timing before the timing (N). A medical image 48 at a timing T(N-S) is an image acquired at a timing before the timing T(N-Q). In the respective medical images, the identical region of interest 44 is detected by the region-of-interest detection unit 41. In the following, the display of the region-of-interest detection results in response to a movement of the region of interest 44 to the upper right, the center portion, and the lower left will be described.

Note that N, Q, and S are natural numbers greater than or equal to 2, where N is larger than Q and S and S is larger than Q. The first display region 34a of the monitor 34 is a region located in a center portion of the monitor 34 to display a medical image. A second display region 34b of the monitor 34 is a display region different from the first display region 34a and is a region for displaying various types of diagnostic information and so on.

Figure 5:
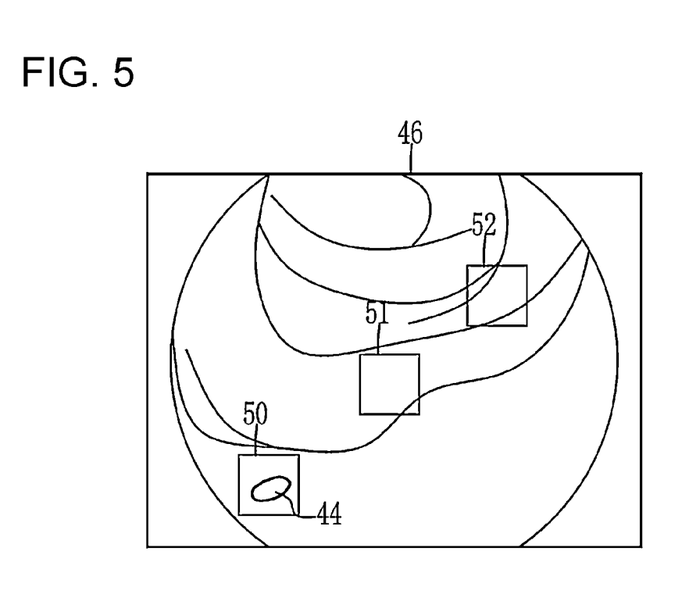
FIG. 5 is an explanatory diagram illustrating, when a region of interest is present in a medical image, bounding boxes displayed at detection positions of the region of interest for a certain period of time.

In a first embodiment, a region-of-interest detection result is displayed as a region-of-interest geometric shape representing the region-of-interest detection result as a geometric shape including at least the region of interest. Examples of the region-of-interest geometric shape include a rectangular bounding box. As illustrated in FIG. 5, in the medical image 46 at the timing T(N), a bounding box 50 displayed so as to surround the region of interest 44 detected at a lower left position (detection position) is displayed. In the medical image 46, in addition to the bounding box 50, a bounding box 51 indicating that the region of interest 44 is detected at a center position (detection position) at the timing T(N-Q), and a bounding box 52 indicating that the region of interest 44 is detected at an upper right position (detection position) at the timing T(N-S) are continuously displayed. The bounding boxes 50, 51, and 52 are continuously displayed for a certain period of time after the detection of the region of interest 44, and thereafter the display of the bounding boxes 50, 51, and 52 is erased in order of the times of detection of the region of interest 44. That is, the bounding box 52 is first erased, followed by the bounding box 51, and the bounding box 50 is finally erased.

Figure 6:
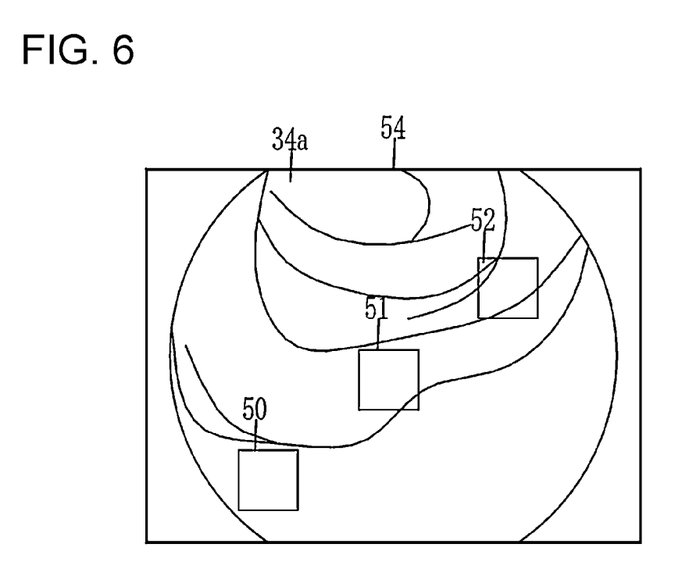
FIG. 6 is an image diagram illustrating, when the region of interest disappears from the medical image, the bounding boxes displayed at the detection positions of the region of interest for a certain period of time.

As described above, not only the bounding box 50 indicating the most recent detection result but also the bounding boxes 51 and 52 indicating the previous detection results are continuously displayed such that the bounding boxes 51 and 52 are displayed at positions where the region of interest 44 is detected. Thus, even if the region of interest 44 disappears instantaneously, it is possible to prevent the user from overlooking the region of interest 44. In addition, since bounding boxes disappear from the screen in order of the times of detection of the region of interest 44, it is possible to intuitively grasp the movement of the region of interest 44. Furthermore, as illustrated in FIG. 6, in a medical image 54 at a timing T(N+M) after the timing T(N), even when the region of interest 44 disappears from the first display region 34a of the monitor 34, the bounding boxes 50, 51, and 52 indicating the results of detection of the region of interest 44 are continuously displayed for a certain period of time. This allows the user to grasp in which direction the region of interest 44 disappears.

Figure 7:
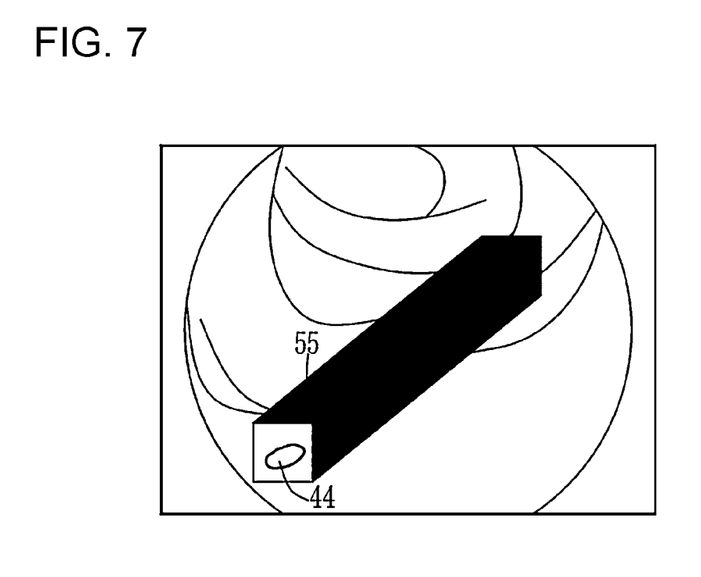
FIG. 7 is an image diagram of a medical image showing continuous display of a bounding box.
Figure 8:
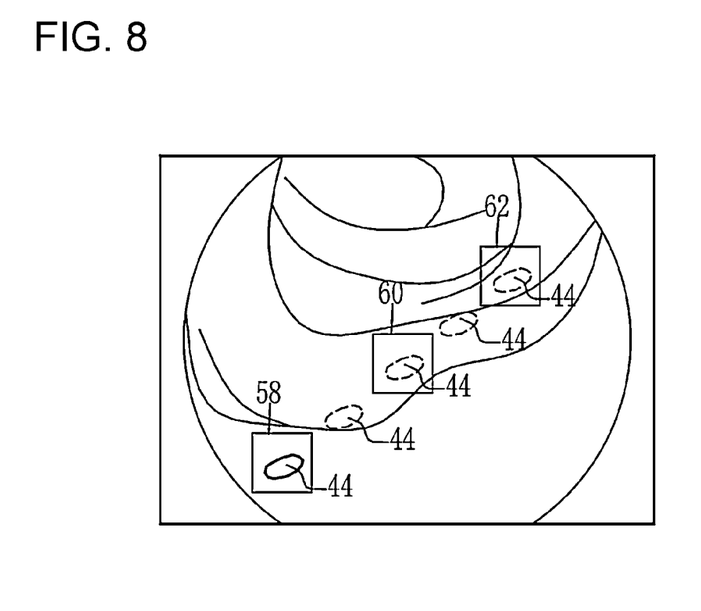
FIG. 8 is an image diagram of a medical image displaying bounding boxes only at specific detection positions among a plurality of detection positions, with some of the detection positions omitted.

The time interval of detection performed by the region-of-interest detection unit 41 may be shortened, and bounding boxes may be displayed at the respective detection positions for a certain period of time to provide continuous display of a bounding box 55 in a manner illustrated in FIG. 7. This makes it possible to clearly grasp the movement direction of the region of interest 44. However, the continuous display of a bounding box may make the photographic subject image in the corresponding portion difficult to see (make the field of view obstructed). To address this, as illustrated in FIG. 8, even when the region-of-interest detection unit 41 detects the region of interest 44 at five positions, some of the detected five detection positions are omitted, and bounding boxes 58, 60, and 62 are displayed only at specific detection positions for a certain period of time. This makes it possible to grasp the movement direction of the region of interest 44 while also grasping the photographic subject image.

Figure 9:
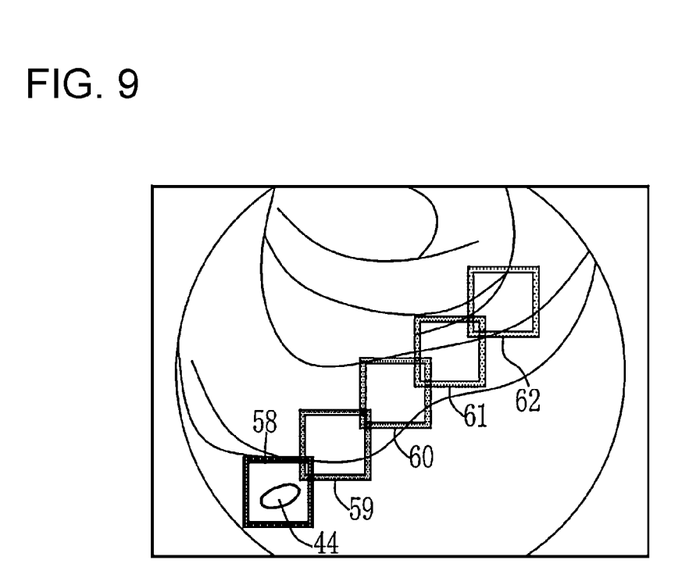
FIG. 9 is an image diagram of a medical image in which the density of the frames of bounding boxes is changed according to the detection timing of the region of interest.

In addition, as described above, when a bounding box is kept displayed for a certain period of time, the display style of the region-of-interest geometric shape may be changed according to the timing at which the region-of-interest detection unit 41 detects the region of interest. As the display style of the region-of-interest geometric shape, for example, the density of the line, or frame, of the bounding box (the degree of highlighting of the line) may be changed. For example, as illustrated in FIG. 9, when, in addition to the bounding box 58 indicating the detection result at the timing T(N), a bounding box 59 indicating a detection result at a timing T(N-P), the bounding box 60 indicating the detection result at the timing T(N-Q), a bounding box 61 indicating a detection result at a timing T(N-R), and the bounding box 62 indicating the detection result at the timing T(N-S) are displayed in the medical image 46 at the timing T(N), the density of the frame of the bounding box 58 for the earliest timing T(N) is set to be the highest, and the density of the frame of the bounding box 59 for the timing T(N-P) before the timing T(N) is set to be lower than the density of the frame of the bounding box 58.

Further, the density of the frame of the bounding box 60 for the timing T(N-Q) before the timing T(N-P) is set to be lower than the density of the frame of the bounding box 59. Further, the density of the frame of the bounding box 61 for the timing T(N-R) before the timing T(N-Q) is set to be lower than the density of the frame of the bounding box 60. Further, the density of the frame of the bounding box 62 for the timing T(N-S) before the timing T(N-R) is set to be lower than the density of the frame of the bounding box 61. As described above, reducing the density of the frame of a bounding box indicating a detection result obtained at a temporally previous timing makes it possible to prevent the photographic subject image from being difficult to see due to the presence of the bounding box (prevent the field of view from being obstructed).

Figure 10:
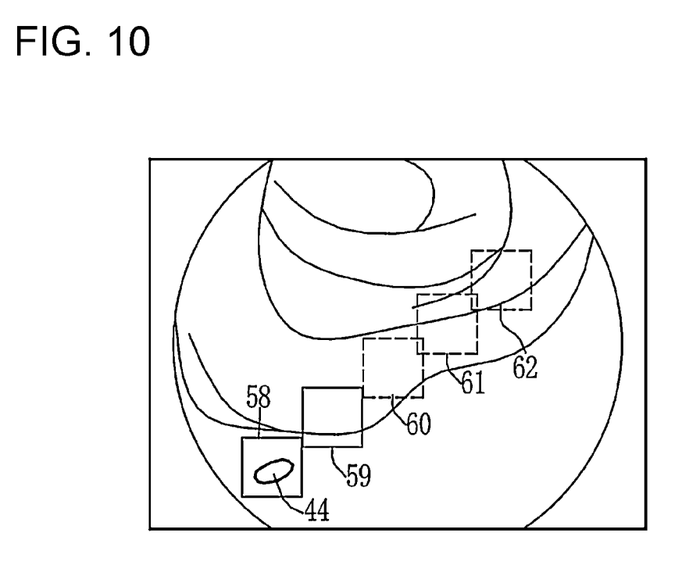
FIG. 10 is an image diagram of a medical image in which the display style of the bounding boxes is changed according to the detection timing of the region of interest.

In addition, as described above, when a bounding box is kept displayed for a certain period of time, the shape of the region-of-interest geometric shape representing the region-of-interest detection result as a geometric shape, such as the bounding box, may be changed according to the timing at which the region-of-interest detection unit 41 detects the region of interest. For example, as illustrated in FIG. 10, when a bounding box is used as a region-of-interest geometric shape, the frames of the bounding box 58 indicating the detection result at the timing T(N) and the bounding box 59 indicating the detection result at the timing T(N-P) may be represented by solid lines, whereas the frames of the bounding boxes 60, 61, and 62 indicating the detection results at the timings T(N-Q), T(N-R), and T(N-S) before the timing T(N-P), respectively, may be represented by broken lines. As described above, the frame of a bounding box indicating a detection result obtained at a temporally previous timing is represented by a broken line, thereby making it possible to prevent the photographic subject image from being difficult to see due to the presence of the bounding box (prevent the field of view from being obstructed).

Figure 11:
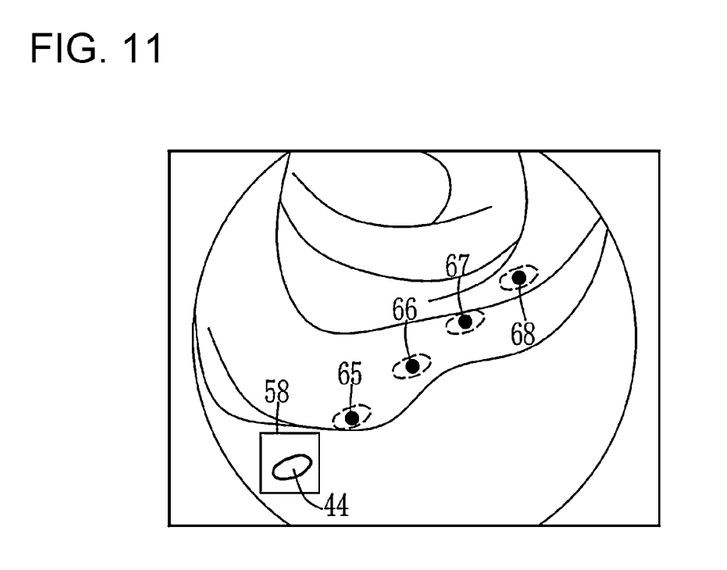
FIG. 11 is an image diagram of a medical image in which the shape of region-of-interest geometric shapes is changed according to the detection timing of the region of interest.

For example, as illustrated in FIG. 11, the detection result at the timing T(N) may be displayed as a region-of-interest geometric shape using the rectangular bounding box 58, whereas the detection results at the timings T(N-P), T(N-Q), T(N-R), and T(N-S) before the timing T(N) may be displayed as region-of-interest geometric shapes using black dots 65, 66, 67, and 68, respectively. As described above, a detection result obtained at a temporally previous timing is displayed using a black dot requiring a small display space rather than using a bounding box requiring a large display space, thereby making it possible to prevent the photographic subject image from being difficult to see (prevent the field of view from being obstructed).

In the first embodiment, as a pattern for changing the display style of a region-of-interest geometric shape according to the timing at which the region-of-interest detection unit 41 detects the region of interest, the size or color of the region-of-interest geometric shape may be changed in addition to the pattern described above. As a pattern for changing the size of the region-of-interest geometric shape, for example, the later the timing of detection of the region of interest, the smaller the size of a region-of-interest geometric shape among region-of-interest geometric shapes to be kept displayed for a certain period of time. As a pattern for changing the color of the region-of-interest geometric shape, for example, the later the timing of detection of the region of interest, the closer to the color component of the medical image (the color component of the photographic subject image such as a mucous membrane) the color component of a region-of-interest geometric shape among region-of-interest geometric shapes to be kept displayed for a certain period of time. In the first embodiment, furthermore, a combination of at least two or more of the size, color, shape, line, or the like of the region-of-interest geometric shape may be changed according to the detection timing of the region of interest.

Second Embodiment

In the first embodiment, the display style of a region-of-interest detection result is a region-of-interest geometric shape, whereas in a second embodiment, the display style of a region-of-interest detection result is region-of-interest highlighting for highlighting the region of interest. In the second embodiment, pseudo-color highlighting for highlighting the region of interest in pseudo-color is used as region-of-interest highlighting. Alternatively, any other highlighting method may be used. Examples of the other highlighting method include superimposition display processing for superimposing a specific region on the region of interest, processing for changing a color tone or gradation, and frequency emphasis processing.

Figure 12:
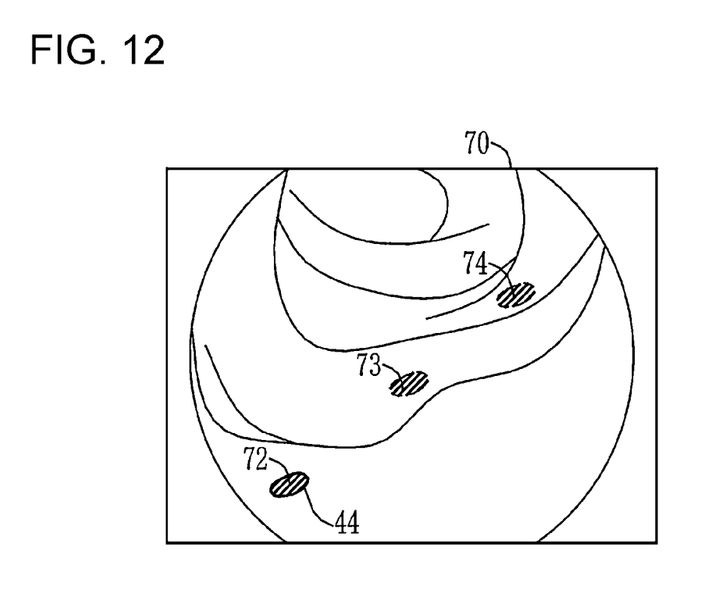
FIG. 12 is an explanatory diagram illustrating pseudo-color highlighted objects displayed for a certain period of time when a region of interest is present in a medical image.

As illustrated in FIG. 12, in a medical image 70 at the timing T(N), a pseudo-color highlighted object 72 that surrounds the region of interest 44 is displayed as a region-of-interest detection result indicating that the region of interest 44 is detected at the lower left position (detection position). In the medical image 70, in addition to the pseudo-color highlighted object 72, a pseudo-color highlighted object 73 indicating that the region of interest 44 is detected at the center position (detection position) at the timing T(N-Q), and a pseudo-color highlighted object 74 indicating that the region of interest 44 is detected at the upper right position (detection position) at the timing T(N-S) are continuously displayed. The pseudo-color highlighted objects 72, 73, and 74 are continuously displayed for a certain period of time after the detection of the region of interest 44. After that, the pseudo-color highlighted objects 72, 73, and 74 are erased.

As described above, not only the pseudo-color highlighted object 72 indicating the most recent detection result but also the pseudo-color highlighted objects 73 and 74 indicating the previous detection results are continuously displayed. Thus, even if the region of interest 44 disappears instantaneously, it is possible to prevent the user from overlooking the region of interest 44 and to grasp the direction of disappearance of the region of interest 44.

Figure 13:
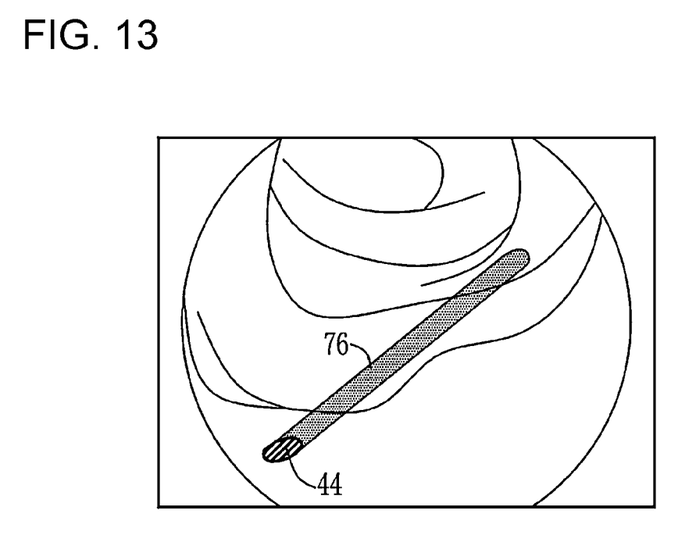
FIG. 13 is an explanatory diagram illustrating a pseudo-color highlighted object continuously displayed for a certain period of time when the region of interest is present in the medical image.
Figure 14:
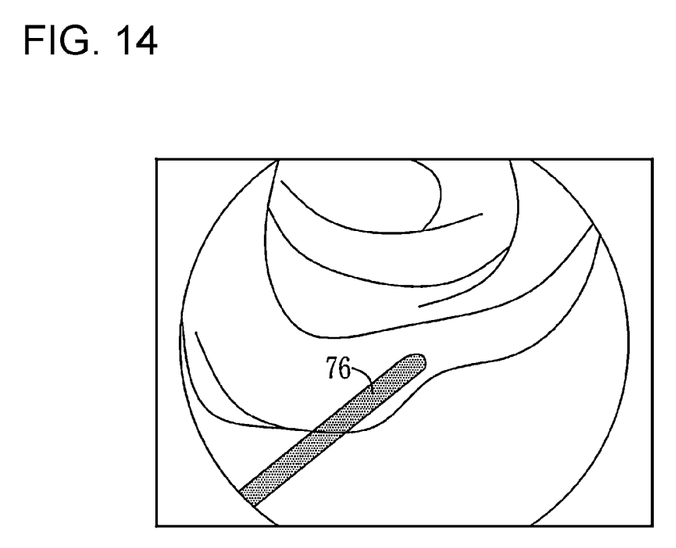
FIG. 14 is an explanatory diagram illustrating a pseudo-color highlighted object continuously displayed for a certain period of time when the region of interest disappears from the medical image.

Furthermore, the time interval of detection performed by the region-of-interest detection unit 41 may be shortened, and pseudo-color highlighted objects may be displayed at the respective detection positions for a certain period of time to provide continuous display of a pseudo-color highlighted object 76 in a manner illustrated in FIG. 13. This makes it possible to clearly grasp the movement direction of the region of interest 44. In addition, even if the region of interest 44 disappears from the first display region 34a of the monitor 34, as illustrated in FIG. 14, the continuous display of the pseudo-color highlighted object 76 makes it possible to not only prevent the user from overlooking the region of interest 44 but also allow the user to grasp in which direction the region of interest 44 disappears.

Figure 15:
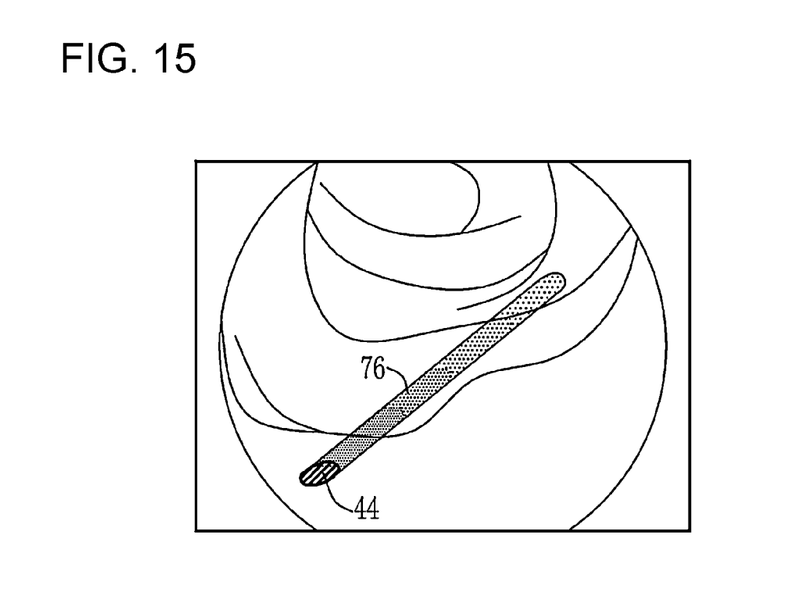
FIG. 15 is an image diagram of a medical image in which the degree of highlighting of a pseudo-color highlighted object is changed according to the detection timing of the region of interest.

However, the continuous display of a pseudo-color highlighted object may make it difficult to see the photographic subject image in the corresponding portion. Accordingly, to grasp the movement direction of the region of interest 44 while grasping the photographic subject image, the display style of the pseudo-color highlighted object may be changed according to the timing at which the region-of-interest detection unit 41 detects the region of interest 44. For example, the larger the distance from the region of interest 44, the earlier the timing at which the region of interest 44 is detected is. Thus, as illustrated in FIG. 15, the degree of highlighting (the density of the pseudo-color highlighted object) of a portion of the continuously displayed pseudo-color highlighted object 76 closer to the region of interest 44 becomes higher, whereas the degree of highlighting of a portion thereof farther away from the region of interest 44 becomes lower. In the second embodiment, the degree of highlighting of the pseudo-color highlighted object is changed according to the detection timing of the region of interest 44. Alternatively, the degree of highlighting or the color proportion of the region-of-interest highlighting may be changed according to the detection timing of the region of interest 44.

Accordingly, it is possible to prevent a photographic subject image from being difficult to see due to pseudo-color highlighting while making it possible to intuitively grasp the movement of the region of interest 44. Instead of changing the degree of highlighting of the pseudo-color highlighted object according to the timing at which the region-of-interest detection unit 41 detects the region of interest 44 in the manner illustrated in FIG. 15, the color component of the pseudo-color highlighted object may be changed. In this case, for example, a portion of the pseudo-color highlighted object closer to the region of interest has a larger proportion of the color component of the pseudo-color (the color far from the color of the photographic subject image), whereas a portion thereof farther away from the region of interest has a smaller proportion of the color component of the pseudo-color to be closer to the color component of the photographic subject image.

Figure 16:
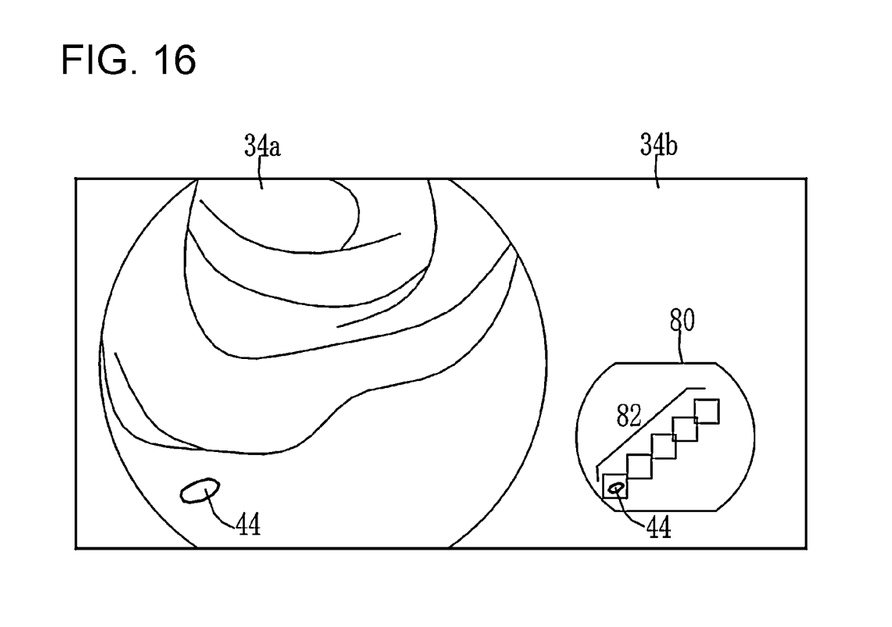
FIG. 16 is an image diagram of a monitor showing bounding boxes displayed in a second display region.

In the first and second embodiments described above, a region-of-interest detection result is displayed in the first display region 34a of the monitor 34. Alternatively, a region-of-interest detection result may not be displayed in the first display region 34a, but may be displayed in the second display region 34b. For example, as illustrated in FIG. 16, the second display region 34b may be provided with a sub-screen 80 in which the region of interest 44 is displayed and bounding boxes 82 indicating region-of-interest detection results are displayed for a certain period of time. Accordingly, appropriately checking the sub-screen 80 of the second display region 34b while observing the photographic subject image in the first display region 34a makes it possible to notice that the region of interest is overlooked and to grasp the movement of the region of interest. The bounding boxes 82 are displayed in such a way as to be kept displayed for a certain period of time after the detection of the region of interest, as in the first embodiment. The sub-screen 80 may display, in addition to the region of interest 44, a medical image including a photographic subject image.

When a region-of-interest detection result is to be displayed in the second display region 34b, region-of-interest geometric shapes such as the bounding boxes 82 may be displayed, or the region-of-interest detection result may be displayed using region-of-interest highlighting such as in pseudo-color. A region-of-interest detection result may be displayed in a monitor (not illustrated) different from the monitor 34, instead of the second display region 34b. In this case, the region-of-interest detection result is transmitted from the endoscope system 21 to the other monitor.

Figure 17:
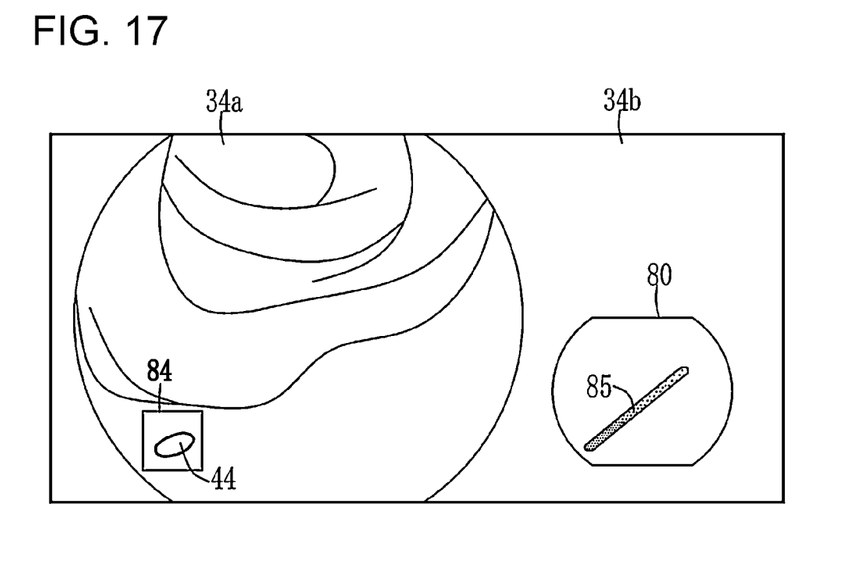
FIG. 17 is an image diagram of a monitor showing a bounding box displayed in a first display region and a pseudo-color highlighted object displayed in the second display region.

Alternatively, a region-of-interest detection result may be displayed in both the first display region 34a and the second display region 34b. For example, as illustrated in FIG. 17, while a bounding box 84 is displayed as a region-of-interest detection result in the first display region 34a, continuous display of a pseudo-color highlighted object 85 is shown in the sub-screen 80 of the second display region 34*b*. The sub-screen 80 displays only a pseudo-color highlighted object without displaying the region of interest 44, which eliminates extra information other than the movement of the region of interest. This allows the user to easily grasp the movement of the region of interest. The first display region 34*a* may be subjected to region-of-interest highlighting, and the second display region 34*b* may display a region-of-interest geometric shape such as a bounding box.

Figure 18:
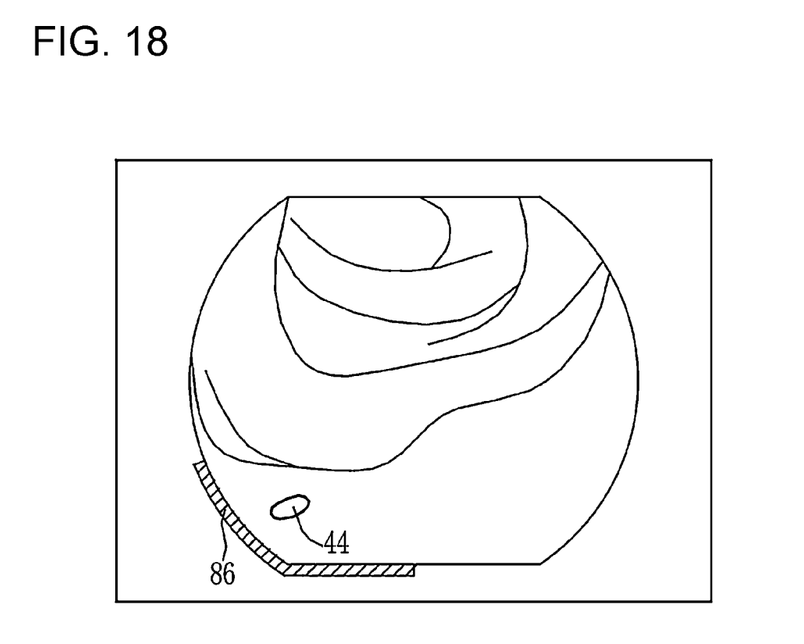
FIG. 18 is an image diagram of a monitor showing a bar displayed in a lower left outer peripheral portion of the first display region.

In the first and second embodiments described above, a region-of-interest detection result is displayed in the first display region 34*a* of the monitor 34. Alternatively, no region-of-interest detection result may be displayed in the first display region 34*a*, and a region-of-interest detection result may be displayed in an outer peripheral portion of the first display region 34*a*. For example, as illustrated in FIG. 18, a detection display bar 86 indicating a region-of-interest detection result may be displayed along a lower left outer peripheral portion in the outer peripheral portion of the first display region 34*a* corresponding to the lower left position at which the region of interest 44 is detected. The detection display bar 86 is continuously displayed for a certain period of time after the region of interest 44 is detected.

Accordingly, it is possible to prevent the user from overlooking the region of interest 44, and, even if the region of interest 44 disappears from the first display region 34*a*, the user is able to intuitively grasp the direction of disappearance of the region of interest 44. In addition, the detection display bar 86 is not displayed in the first display region 34*a* where the user's line of sight is concentrated, thereby preventing the user from being disturbed while observing the region of interest 44. Additionally, the detection display bar 86 is displayed in the outer peripheral portion of the first display region 34*a*, thereby reducing the movement of the line of sight of the user. In addition to displaying a region-of-interest detection result in the outer peripheral portion of the first display region 34*a*, the region-of-interest detection result may be displayed in the first display region 34*a* for a certain period of time, or the region-of-interest detection result may be displayed in the second display region 34*b* for a certain period of time. When a region-of-interest detection result is to be kept displayed for a certain period of time in the outer peripheral portion of the first display region 34*a*, the region-of-interest detection result in the first display region 34*a* may not be kept displayed. In this case, it is possible to prevent the region of interest from being overlooked while reducing disturbance with the user's diagnosis using the medical image in the first display region 34*a*.

Figure 19:
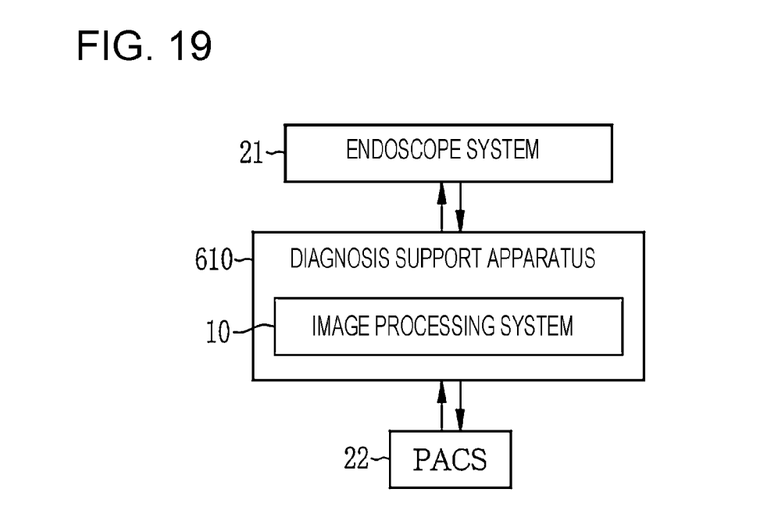
FIG. 19 is a schematic diagram illustrating a diagnosis support apparatus including the image processing system.
Figure 20:
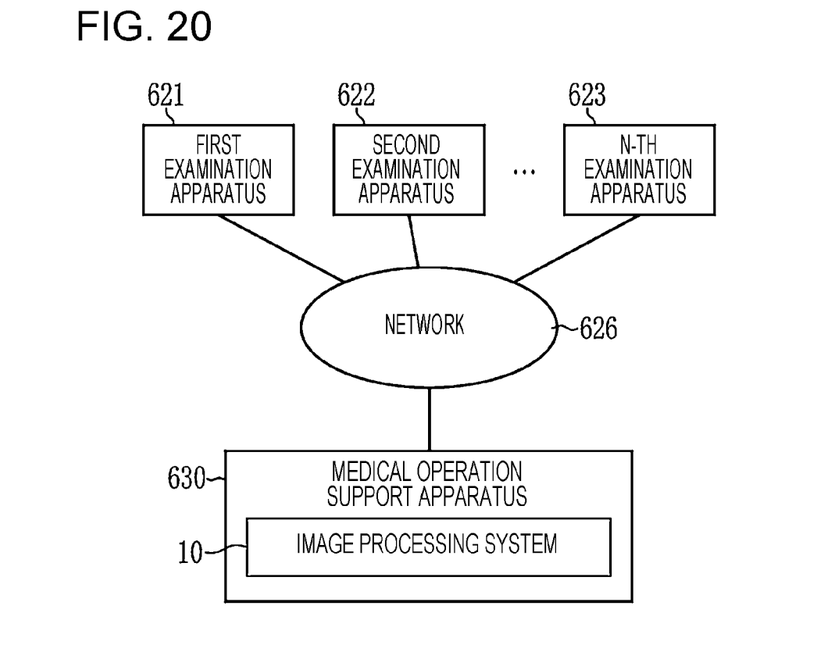
FIG. 20 is a schematic diagram illustrating a medical operation support apparatus including the image processing system.

As illustrated in FIG. 19, a diagnosis support apparatus 610 to be used in combination with the endoscope system 21 or any other modality and the PACS 22 can include the image processing system 10 according to the embodiments described above and other modifications. As illustrated in FIG. 20, for example, a medical operation support apparatus 630 including the endoscope system 21 and to be connected to various examination apparatuses such as a first examination apparatus 621, a second examination apparatus 622, . . . , and an N-th examination apparatus 623 via a desired network 626 can include the image processing system 10 according to the embodiments described above and other modifications.

Additionally, the image processing system 10, the endoscope system 21, and various apparatuses or systems including the image processing system 10 can be used with various modifications or the like described below.

As the medical image, a normal light image obtained by irradiation with light in the white range or, as light in the white range, light in a plurality of wavelength ranges.

When an image obtained by irradiation with light in a specific wavelength range is used as the medical image, the specific wavelength range may be a range narrower than the white wavelength range.

The specific wavelength range is, for example, the blue range or green range in the visible range.

When the specific wavelength range is the blue range or green range in the visible range, preferably, the specific wavelength range includes a wavelength range greater than or equal to 390 nm and less than or equal to 450 nm or greater than or equal to 530 nm and less than or equal to 550 nm, and light in the specific wavelength range has a peak wavelength in a wavelength range greater than or equal to 390 nm and less than or equal to 450 nm or greater than or equal to 530 nm and less than or equal to 550 nm.

The specific wavelength range is, for example, the red range in the visible range.

When the specific wavelength range is the red range in the visible range, preferably, the specific wavelength range includes a wavelength range greater than or equal to 585 nm and less than or equal to 615 nm or greater than or equal to 610 nm and less than or equal to 730 nm, and light in the specific wavelength range has a peak wavelength in a wavelength range greater than or equal to 585 nm and less than or equal to 615 nm or greater than or equal to 610 nm and less than or equal to 730 nm.

The specific wavelength range may include, for example, a wavelength range in which a light absorption coefficient is different between oxyhemoglobin and reduced hemoglobin, and light in the specific wavelength range may have a peak wavelength in a wavelength range in which a light absorption coefficient is different between oxyhemoglobin and reduced hemoglobin.

When the specific wavelength range includes a wavelength range in which a light absorption coefficient is different between oxyhemoglobin and reduced hemoglobin, and light in the specific wavelength range has a peak wavelength in a wavelength range in which a light absorption coefficient is different between oxyhemoglobin and reduced hemoglobin, preferably, the specific wavelength range includes a wavelength range of 400±10 nm, 440±10 nm, 470±10 nm, or greater than or equal to 600 nm and less than or equal to 750 nm, and light in the specific wavelength range has a peak wavelength in a wavelength range of 400±10 nm, 440±10 nm, 470±10 nm, or greater than or equal to 600 nm and less than or equal to 750 nm.

When the medical image is an in-vivo image obtained by imaging of the inside of a living body, the in-vivo image may have information on fluorescence emitted from a fluorescent substance in the living body.

As the fluorescence, fluorescence obtained by irradiation of the inside of a living body with excitation light having a peak wavelength greater than or equal to 390 nm and less than or equal to 470 nm may be used.

When the medical image is an in-vivo image obtained by imaging of the inside of a living body, the wavelength range of infrared light may be used as the specific wavelength range described above.

When the medical image is an in-vivo image obtained by imaging of the inside of a living body and the wavelength range of infrared light is used as the specific wavelength range described above, preferably, the specific wavelength range includes a wavelength range greater than or equal to 790 nm and less than or equal to 820 nm or greater than or equal to 905 nm and less than or equal to 970 nm, and light in the specific wavelength range has a peak wavelength in a wavelength range greater than or equal to 790 nm and less than or equal to 820 nm or greater than or equal to 905 nm and less than or equal to 970 nm.

The medical image acquisition unit 11 can have a special light image acquisition unit that acquires a special light image having a signal in the specific wavelength range on the basis of a normal light image obtained by irradiation with light in the white range or, as light in the white range, light in a plurality of wavelength ranges. In this case, the special light image can be used as the medical image.

The signal in the specific wavelength range can be obtained by calculation based on color information of RGB or CMY included in the normal light image.

A feature value image generation unit can be included that generates a feature value image by using calculation based on at least one of a normal light image obtained by irradiation with light in the white range or, as light in the white range, light in a plurality of wavelength ranges and a special light image obtained by irradiation with light in the specific wavelength range. In this case, the feature value image can be used as the medical image.

In the endoscope system 21, a capsule endoscope can be used as the endoscope 31. In this case, the light source device 32 and a portion of the processor device 33 can be mounted in the capsule endoscope.

In the embodiments described above and modifications, the hardware structure of processing units that execute various types of processing, such as the medical image acquisition unit 11, the medical image analysis processing unit 12, the display control unit 15, the input receiving unit 16, the overall control unit 17, the medical image acquisition unit 35, the medical image analysis processing unit 36, the display control unit 37, and the region-of-interest detection unit 41, is implemented as various processors described hereinbelow. The various processors include a CPU (Central Processing Unit), which is a general-purpose processor executing software (program) to function as various processing units, a programmable logic device (PLD) such as an FPGA (Field Programmable Gate Array), which is a processor whose circuit configuration is changeable after manufacture, a dedicated electric circuit, which is a processor having a circuit configuration specifically designed to execute various types of processing, a GPU (Graphical Processing Unit), and so on.

A single processing unit may be configured as one of the various processors or as a combination of two or more processors of the same type or different types (for example, a plurality of FPGAs, a combination of a CPU and an FPGA, or a combination of a CPU and a GPU). Alternatively, a plurality of processing units may be configured as a single processor. Examples of configuring a plurality of processing units as a single processor include, first, a form in which, as typified by a computer such as a client or a server, the single processor is configured as a combination of one or more CPUs and software and the processor functions as the plurality of processing units. The examples include, second, a form in which, as typified by a system on chip (SoC) or the like, a processor is used in which the functions of the entire system including the plurality of processing units are implemented as one IC (Integrated Circuit) chip. As described above, the various processing units are configured by using one or more of the various processors described above as a hardware structure.

More specifically, the hardware structure of these various processors is an electric circuit (circuitry) in which circuit elements such as semiconductor elements are combined.

Another embodiment of the present invention provides a medical image processing system in which a processor device acquires, using a medical image acquisition unit, a medical image obtained by imaging of an observation target, detects, using a region-of-interest detection unit, a region of interest from the medical image, and keeps displaying of, using a display control unit, a detection result of the region of interest for a certain period of time on a display unit, in a case where a position of the region of interest is changed in accordance with a movement of the region of interest, at a detection position of the region of interest detected by the region-of-interest detection unit before the position of the region of interest is changed.

REFERENCE SIGNS LIST 10 image processing system
11 medical image acquisition unit
12 medical image analysis processing unit
13 display unit
15 display control unit
16 input receiving unit
17 overall control unit
18 storage unit
21 endoscope system
22 PACS
31 endoscope
32 light source device
33 processor device
34 monitor
34a first display region
34b second display region
35 medical image acquisition unit
36 medical image analysis processing unit
37 display control unit
41 region-of-interest detection unit
44 region of interest
46 medical image
47 medical image
48 medical image
50, 51, 52 bounding box
54 medical image
55, 58, 59, 60, 61, 62 bounding box
65, 66, 67, 68 black dot
70 medical image
72, 73, 74, 76 pseudo-color highlighted object
80 sub-screen
82, 84 bounding box
85 pseudo-color highlighted object
86 detection display bar
610 diagnosis support apparatus
621 first examination apparatus
622 second examination apparatus
623 N-th examination apparatus
626 network
630 medical operation support apparatus

What is claimed is:
1. A medical image processing system comprising:
a processor configured to function as:
a medical image acquisition unit that acquires a medical image obtained by imaging of an observation target of a living body, wherein the medical image is an image obtained by using an endoscope;

a region-of-interest detection unit that detects a region of interest from the medical image; and a display control unit that keeps displaying a plurality of detection results of the region of interest for a certain period of time on a display, in a case where a position of each of the plurality of detection results of the region of interest is changed so as to form a movement path of the region of interest, at a detection position of the region of interest detected by the region-of-interest detection unit before the position of the region of interest is changed, wherein at least a most recent detection result of the region of interest and a previous detection result of the region of interest among the plurality of detection results are simultaneously displayed on the display, wherein a display style of the plurality of detection results of the region of interest is a region-of-interest geometric shape representing the detection result of the region of interest as a geometric shape surrounding the region of interest.

2. The medical image processing system according to claim 1, wherein the display control unit keeps displaying the plurality of detection results of the region of interest for a certain period of time at a specific detection position among detection positions of the region of interest.

3. The medical image processing system according to claim 1, wherein the display control unit changes a display style of the plurality of detection results of the region of interest according to a timing at which the region of interest is detected.

4. The medical image processing system according to claim 3, wherein the display control unit changes a display style of the region-of-interest geometric shape according to the timing at which the region of interest is detected.

5. The medical image processing system according to claim 4, wherein the display style of the region-of-interest geometric shape includes a shape, a size, or a color of the region-of-interest geometric shape or a line of the region-of-interest geometric shape.

6. The medical image processing system according to claim 3, wherein the display style of the plurality of detection results of the region of interest is region-of-interest highlighting for highlighting the region of interest, and wherein the display control unit changes a degree of highlighting for the region-of-interest highlighting according to the timing at which the region of interest is detected.

7. The medical image processing system according to claim 6, wherein the region-of-interest highlighting includes pseudo-color highlighting for highlighting the region of interest in pseudo-color, and wherein the display control unit changes the degree of highlighting for the region-of-interest highlighting or a proportion of a color component of the region-of-interest highlighting according to the timing at which the region of interest is detected.

8. The medical image processing system according to claim 1, wherein the display control unit displays the plurality of detection results of the region of interest in at least one of a first display region of the display that displays the medical image or a second display region different from the first display region of the display that displays the medical image.

9. The medical image processing system according to claim 8, wherein a display style of the plurality of detection results of the region of interest displayed in the first display region is identical to or different from a display style of the detection result of the region of interest displayed in the second display region.

10. The medical image processing system according to claim 1, wherein the display control unit displays the plurality of detection results of the region of interest in a portion of an outer peripheral portion of a first display region of the display that displays the medical image, the portion of the outer peripheral portion being a portion corresponding to the detection position of the region of interest.

11. The medical image processing system according to claim 1, wherein an earliest detection result among the plurality of detection results is erased in an order of time of the detection results of the region of interest.

12. The medical image processing system according to claim 1, wherein a geometric shape of the most recent detection result and a geometric shape of the previous detection result are different.

* * * * *